(12) United States Patent
Kouvonen (10) Patent No.: US 6,379,972 B1
(45) Date of Patent: Apr. 30, 2002

(54) PERFORATING ANALYTICAL TEST DEVICE

(75) Inventor: Ilkka Kouvonen, Kauniainen (FI)

(73) Assignee: Oy Medix Biochemica AB, Kauniainen (FI)

(*) Notice: Subject to any disclaimer, the term of this patent is extended or adjusted under 35 U.S.C. 154(b) by 0 days.

(21) Appl. No.: 09/341,434

(22) PCT Filed: Feb. 13, 1998

(86) PCT No.: PCT/FI98/00134
  § 371 Date: Sep. 9, 1999
  § 102(e) Date: Sep. 9, 1999

(87) PCT Pub. No.: WO98/36259
  PCT Pub. Date: Aug. 20, 1998

(30) Foreign Application Priority Data

Feb. 14, 1997 (FI) ................................................ 970638

(51) Int. Cl.⁷ .............................................. G01N 33/49
(52) U.S. Cl. ...................... 436/169; 436/164; 422/58; 422/61; 422/102
(58) Field of Search ........................... 422/56, 58, 61, 422/100, 102; 436/164, 169, 170, 177, 178, 180

(56) References Cited

U.S. PATENT DOCUMENTS 4,912,755 A * 3/1990 Blood et al. .................... 329/6
5,054,499 A * 10/1991 Swierczek .................. 128/770

FOREIGN PATENT DOCUMENTS

| WO | 86 05966 | 10/1986 |
| WO | 93 09431 | 5/1993 |
| WO | 96 01890 | 1/1996 |

OTHER PUBLICATIONS

"CheckCup," Applied Biotech, Inc. marketing brochure, No. 10–5100–A.
"StatusCup Plus," LifeSign marketing brochure, May 11, 2001, Somerset, NJ.

* cited by examiner

Primary Examiner—Lyle A. Alexander
(74) Attorney, Agent, or Firm—Birch, Stewart, Kolasch & Birch, LLP (57) ABSTRACT

An analytical test device and method of use are taught. The device has a perforating sharp tip to contact the sample. The tip has an aperture permitting the sample to flow into a recess of the device without the application of vacuum. In the recess is a test means that is contacted by the sample flowing through the aperture and give the test results.

20 Claims, 10 Drawing Sheets

PERFORATING ANALYTICAL TEST DEVICE

This application is the national phase under 35 U.S.C. §371 of PCT International Application No. PCT/FI99/00134 which has an International filing date of Feb. 13, 1998 which designated the United States of America.

THE TECHNICAL FIELD OF THE INVENTION

The present invention is related to a perforating analytical test device for hygienic and risk-free handling of hazardous samples comprising a test stick, which is placed in or can be placed into the device, which is capable of penetrating the sampling vessel or the stopper thereof without the need of opening the stopper of the sampling vessel.

THE BACKGROUND OF THE INVENTION

Some biological samples, especially those clinical samples which are taken for detection or diagnoses of infectious diseases are dangerous and unpleasant to handle. Fecal samples are not only unpleasant, but in addition to being inconvenient, the handling of the sample can be dangerous, particularly, if the sample contains pathogenic organisms, such as salmonella-, cholerae-, EHEC-bacteria, rotavirus or dysentery causing *Entamoeba histolytica*. In addition to fecal samples, many other types of samples originating from hospitals or medical centers constitute a health risks to those carrying out the test. Samples containing toxic or radioactive substances forms another group of hazardous samples.

Usually, when the test is carried out, the sample vessel or bottle is opened by removing the stopper in a place specially reserved for tests, which might constitute a contamination risk. Test sticks, such as those described in e.g. patent applications EP 284 232, EP 291 194, WO 94/15215 or some other of the multitude of test strip-, dipstick-variants developed during the past decades are then dipped into the sample solution and transferred to a test tube or some other vessel to develop the test results. The test stick is allowed to stand in said vessel until the result is detectable or can be made detectable, either visually or by some apparatus or device capable of reading or monitoring the result. Even if the test is performed with appropriate skill and the utmost care, a contamination risk always exists. When the stoppers of the sampling vessels are removed tiny drops of the sample solution might easily be splashed around and might contaminate the hands or clothes of those carrying out the test as well as the environment in which the test is carried out. When the test stick is transferred from the sampling vessel to the other vessel for developing, drops of the sample solution might drip down on the table or those performing the tests have to use some alternative means to avoid dripping. Consequently, a risk of contamination is always present and wastes, which have to be handled as hazardous waste products are produced. The equipments and means used as well as the environments have to be disinfected and sterilized when the test or tests have been completed.

Sampling rods or swabs or sampling devices which are brought into contact with a developing solution or reacting agents have been described for example in the following patent applications JP 08005627, WO 95/25948, WO 96/28715, GB 1587174. None of the described devices disclose a system wherein a hazardous sample is collected in a sampling vessel and the sampling vessel is transported to another laboratory sometimes even by air. In such cases the sampling vessel must be made of a strong and durable material to resist any accidents during transport. In the laboratory, the sample has generally been handled as described above, but it is not desirable that the person performing the test is exposed to open contact with the hazardous sample. The device of the present invention solves the problem by providing a combined perforating and analytical test device which is capable of perforating a strong and durable, even air-transportable sampling vessel without exposing the person performing the test to open contact with the sample.

SUMMARY OF THE INVENTION

Thus, the objective of the present invention is to provide a combined perforating analytical test device, which decreases the disadvantages connected with the hazardous systems of prior art and diminishes the risk of contamination caused by the removal of stoppers from the vessels and transfer of the test sticks from one vessel to another. At the same time the need of repeated and extensive disinfection measures is decreased and the perforating analytical test device can be destroyed using appropriate measure without exposing the person performing the test, at any time, to any contact with the sample. The purpose of the present invention is above all to protect those performing the test from unnecessary contamination risks and possible inconveniences caused by odors by providing a device, which is easy to handle and enables the test to be carried out without opening the sampling vessel and transferring the test stick to another vessel.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

A BRIEF DESCRIPTION OF THE DRAWINGS

The present invention will become more fully understood from the detailed description given hereinbelow and the accompanying drawings which are given by way of illustration only, and thus are not limitative of the present invention, and wherein.

THE DETAILED DESCRIPTION OF THE INVENTION

Definitions

In the description which follows, most terms are used in the same way they are generally used in diagnostics, immunochemistry and biochemistry. However, some terms are used in a somewhat different or more extensive way. In order to provide a clearer and more consistent understanding of the specification and claims including the scope to be given such terms, the following definitions are given.

The term "sampling vessel" means a bottle, or test tube or some other means into which the sample is collected or into which the samples, in the form of a biopsy item or as the contents from a swab is diluted by the aid of suitable diluents such as water, buffers, etc., to form a "sample solution". The "sampling vessel" is preferably provided with a stopper which can tightly fastened.

The term "stopper" means any sampling vessel closing device, which acts as a lock, cap, etc., and which assures that no leakage of the sample solution can occur, e.g. during transport. The stopper can be snapped or screwed or fastened by any means to the vessel. The stopper can be provided with a region made of a thinner, softer or more elastic material, which is more easily penetrable and said region can further be designed with supports which protects the test stick placed into the perforating analytical device and steadies the hand of the person carrying out the perforation. The most important features of the sampling vessel or the stopper thereof as well as the perforating device are that they are made of a material, which is so elastic and flexible that they together form a water-tight joint, which is so tight and closely fitted or almost glued together that no sample solution can leak or penetrate from the sampling vessel. Thus, the elasticity or flexibility characterizing polyethylene or polypropylene such as polypropylene (PE), high density polyethylene (HD-PE), low density polyethylene (LD-PE) or polypropylene (PP) are advantageous.

By the term "test stick" an elongated analytical device in dip-stick solid-phase format is meant. The test stick can be a test strip placed on or in a solid support or it can be any kind of absorbing stuff incorporated e.g. into a kind of column, the shape of which can vary. The test strip or column comprises the tracers and markers and reagents required for carrying out the analytical test.

The term "hygienic" and "risk-free" means that the system containing the hazardous sample is closed in such a way that the person performing the test is not exposed to open contact with the hazardous material and the contamination risk is diminished and the need of decontamination and sterilizing measures is decreased.

The term "handling" included the optional insertion of the test stick, the perforation, the optional pushing and pulling of the perforating analytical test device or alternatively, turning the vessel upside down and back to upright position in order to avoid a surplus or excess, i.e. a redundant, disturbing absorption of the sample solution.

The term "hazardous" means that the sample contains risk causing materials, such pathogenic disease-causing organisms as well as toxic, corrosive or radioactive substances, which may contaminate the environment and the person handling the material.

The term "tip portion" means the portion, which penetrates and corresponds to the blade of a knife. The term "pointed" means that the tip of the perforating device has a sharp end, which facilitates the penetration. Thus, the "pointed tip" of the tip portion acts like the edge of the knife.

The term "grip portion" means the handle or helve, which is gripped or taken hold of with the hand when the perforation is carried out.

The term "opening" means a hollow room inside the perforating analytical test device for the test stick.

The term "shaped" means formed during the manufacturing e.g. by molding of plastics, or plasticizing.

The term "incorporating" or "incorporated" means that an item has been inserted or placed into the appropriate device.

The term "aperture" means a hole of optional form on the outside wall of the perforating analytical test device.

The term "recess" means an opening on the outside of the device and which passes into the device, i.e. a hole, which is not blocked by the test stick. Thus, the "recess" allows free access of the sample solution into the perforating analytical device and improves the absorbation into the test stick.

The term "absorption" means that the sample solution is taken up in the wetting region of the test stick and transferred or moved by e.g. capillary forces or diffusion into the reagent containing zones or regions of the test strip or test stick.

The term "handle walls" mean the side walls of the grip portion, which can have two separate walls connected by the back wall. Alternatively, they can be form a shaped handle in one piece, which fits the hand of person performing the test. However, it is important that the handle walls, include a niche for the test stick and an easy monitoring or reading of the results is facilitated from the reading zone of the test stick in the niche of the grip portion.

The term "connected" or "connecting" means that a supporting bridge is formed between the handle walls in the grip portion. "Test stick supporting back wall" means said connecting wall, which alternatively can be molded in one piece with the handle walls fitting the hand of the analyser and incorporating a visibly situated place for the reading zone of the test stick.

The term "hold improving means" is used to mean nibbles or protuberances in form of spots or stripes, which aid the grip of the person perforating the sampling vessel or the stopper. Alternatively, the "hold improving means" can be a sand-paper-like, rough structure on the surface of the handle walls in the form of a coating or in situ prepared during molding of the plastic.

"Wetting zone" means the part or region of the test stick, which is contacting the sample solution and contains absorbing material capable of absorbing the sample solution. Preferably said part does not contain any of the reagents incorporated into the test stick.

"Reading zone" means the part or region of the test stick wherein the test results are detectable or can be made detectable either visually or by suitable means. The result is generally readable as, yes or no, depending upon the lines developing or not developing on the reading zone.

"Protruding" means that e.g. the "grip portion" of the device is sticking out in a visible position outside the sampling vessel and the stopper.

The term "package combination" means a kit comprising a set of disposable, ready for use, perforating analytical test devices and/or separate test sticks with perforating devices.

The term "disposable" means that the device is used only once and thereafter destroyed by appropriate means.

The term "desired time" is the time, which is sufficient for the absorbed sample solution to reach the reading zone of the test stick.

The General Description of the Invention

The objective of the invention is made feasible by a perforating analytical test device, having a pointed tip portion and a grip portion. The tip portion comprises a sharp pointed tip prepared by a material, preferably a plastic material, which is sufficiently durable and tough enough to allow the perforation of the sampling vessel or the stopper thereof and to prevent damages to the test stick while the perforation step is carried out. In addition the perforating analytical test device acts as a protector for the test stick during storage and transport. At the same time the material or substance of which the perforating device is made of should be sufficiently elastic to allow the perforating device together with the stopper to form a joint which is so tight that no sample solution can penetrate through the linings of the joint. The inside of the tip portion of the perforating device is provided with an opening, which is shaped so that the test stick used in the analytical test fits exactly into it. The opening runs through the tip portion, but the outmost tip is solid and compact in order to be sufficiently strong and capable of penetrating the sampling vessels or stoppers. The contact between the test stick and the sample solution is made feasible through the apertures on the outer surface of the tip portion of the perforating analytical test device.

Optionally the contact is improved by a recess or a hole which allows the sample solution to flow into the device and wet the test stick. The perforating analytical test device and the test stick should also be capable of forming such a tightly connected combination that no leakage of the sample solution can occur and the sample solution should only be absorbed through the wetting zone into the test stick. No leakage of sample solution should be allowed to occur, even if the vessel is turned upside down.

The test stick can be placed into the perforating analytical test device during the manufacture and sold as a disposable ready for use kit. The test kit can be placed into the perforating analytical test device in such a way that the lower part of the test stick optionally reaches the surface of the sample solution. Alternatively, the lower part of the test stick does not reach the sample solution. In said case, in order to allow the absorption of the sample solution into the test stick, the sampling vessel has to be turned upside down. The grip portion of the perforating device protruding from above the stopper and the grip portion of the perforating device allows the test results to be seen so that the results are easily readable.

The perforating device is pushed through the stopper of the sampling vessel. The stopper can be provided with a region made of a thinner, softer and/or more elastic material and further designed with a supporting structure, which not only supports and protects the test stick, but also assists the person performing the test to direct the pointed tip of the perforator appropriately and to avoid the pointed tip from sliding or slipping on the surface of the stopper. After the perforation, the test stick is allowed to come into contact with the sample solution in the bottom of the vessel.

Optionally the perforator is mobile, i.e. can be pushed and pulled to some extent so that the test stick and the sample solution are not in a continuous contact when the results are developed. Thus, excess or redundant sample solution is prevented from being absorbed into the test stick and possible disturbing the test results.

Consequently, the sample can be analysed without opening the stopper of the sampling vessel. The test stick can also be allowed to come in contact with the sample solution by turning the vessel upside down in which case the wetting zone of the test stick comes in contact with the sample for a short time through the aperture on the surface of the tip portion of the perforating device. The size of the tip of the perforating device is adjusted to the size of the test stick used in the perforating device as well as to the size of the sampling vessel. The size of the aperture on the surface of the tip must not be longer than the wetting zone of the test stick.

The surface of the sample solution in the sampling vessel should absolutely not reach to the zone containing tracers, labelled particles, i.e. reagents. The sample solution should be absorbed through the wetting zone and such an amount of the sample solution should be allowed to be absorbed only in such an amount that it reaches the reading zone. Thereafter, the contact between the test stick and sample solution is preferably broken. The sample solution is absorbed through the aperture through the wetting region and then it flows by capillary forces through the region containing the tracer, i.e. binding substances such as ligands, antibodies and /or antigens, labelled particles, etc., until it reaches the reading zone. As the solution reaches the reading zone the sampling vessel is turned back to its normal upright position and the result is allowed to develop. Accordingly, the wetting zone of the test stick is not more in contact with the sample solution. Thus, a redundant amount of sample solution is prevented from being absorbed into the test stick.

Thereafter, the test is allowed to develop without any possibly disturbing movements until the result is visible. The result is recorded directly, e.g. visually from the test stick protruding above the stopper of the perforating analytical test device according to the invention. Finally, everything including the sample vessel, stopper, perforating device and the test stick can be destroyed by appropriate means, by burning or alternatively sterilization or decontamination before disposing it. The test arrangements assure that the person performing the test is not exposed to open contact with the hazardous sample solution at any point of the analytical proceeding.

The device of the present invention and the use thereof for performing analyses with a test stick is described in more detail by referring to the attached FIGS. 1–10, wherein the reference numbers and/or letters used refer to the corresponding features independent of the design of the perforating analytical test device.

In this connection it should be understood that the following description and Figures are intended to be examples, which should in no way restrict the invention to the specific features shown in the Figures. On the contrary the scope of protection is intended to cover all modifications, equivalencies or alternatives, which contain the characteristics of the device as defined in the claims and include the possibility of making a hygienic test with a test stick without opening the stopper of the sampling vessel using a perforating analytical test device according to the present invention.

Figure 1:
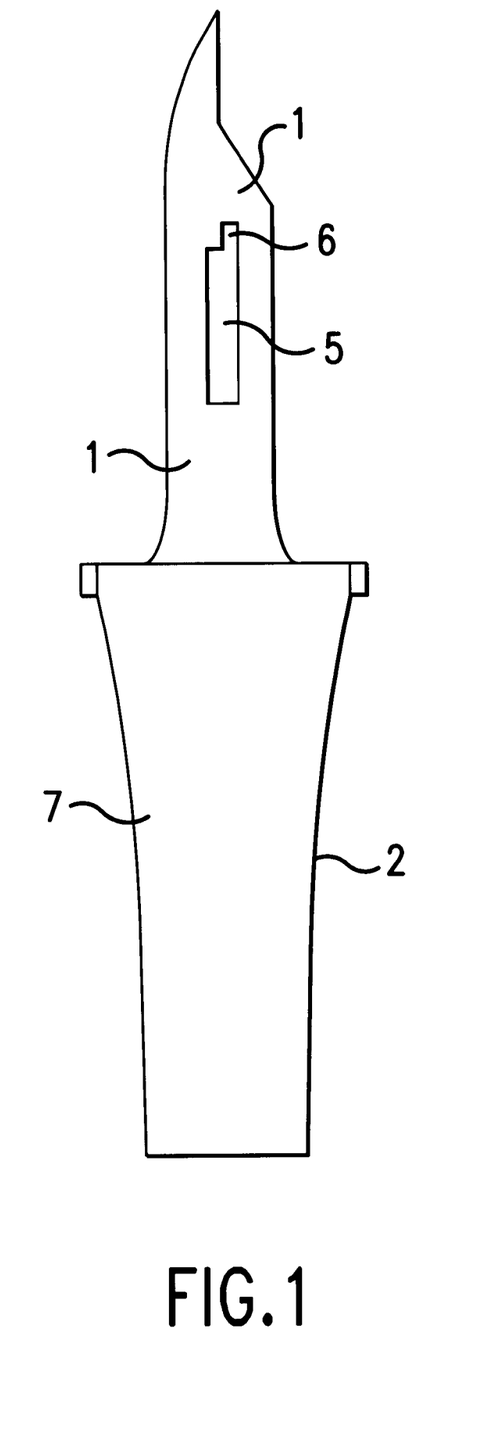
FIG. 1 depicts the perforating analytical test device viewed from one side. The tip portion with the aperture and recess is situated on the outside wall of the tip portion. The side of one of the handle walls of the grip portion is shown in full, whereas the opposite handle is not visible in FIG. 1.

FIG. 1 depicts a side view from the outside of the perforating analytical test device. The perforating analytical test device comprises a tip portion (1) and a grip portion (2). The tip portion (1) comprises a sharp pointed tip, which is produced by a material, preferably of a plastic material, which is sufficiently hard and durable to perforate, pierce or penetrate the sampling vessel or the stopper thereof. The surface of the tip portion (1) is provided with an aperture (5), which continues in a recess (6) into which the test stick cannot reach. The grip portion (2) comprises two opposite handle walls (7), one of which can be seen in FIG. 1. The handle walls (7) can optionally be provided with hold improving means such as protruding spots, nipples and lines, which improve the grip and prevents the hand from slipping when the sampling vessel or stopper is perforated. The surface of the handle wall can also be provided with a sandpaper-like or rough coating or the handle walls can be provided with the structure during molding.

Figure 2:
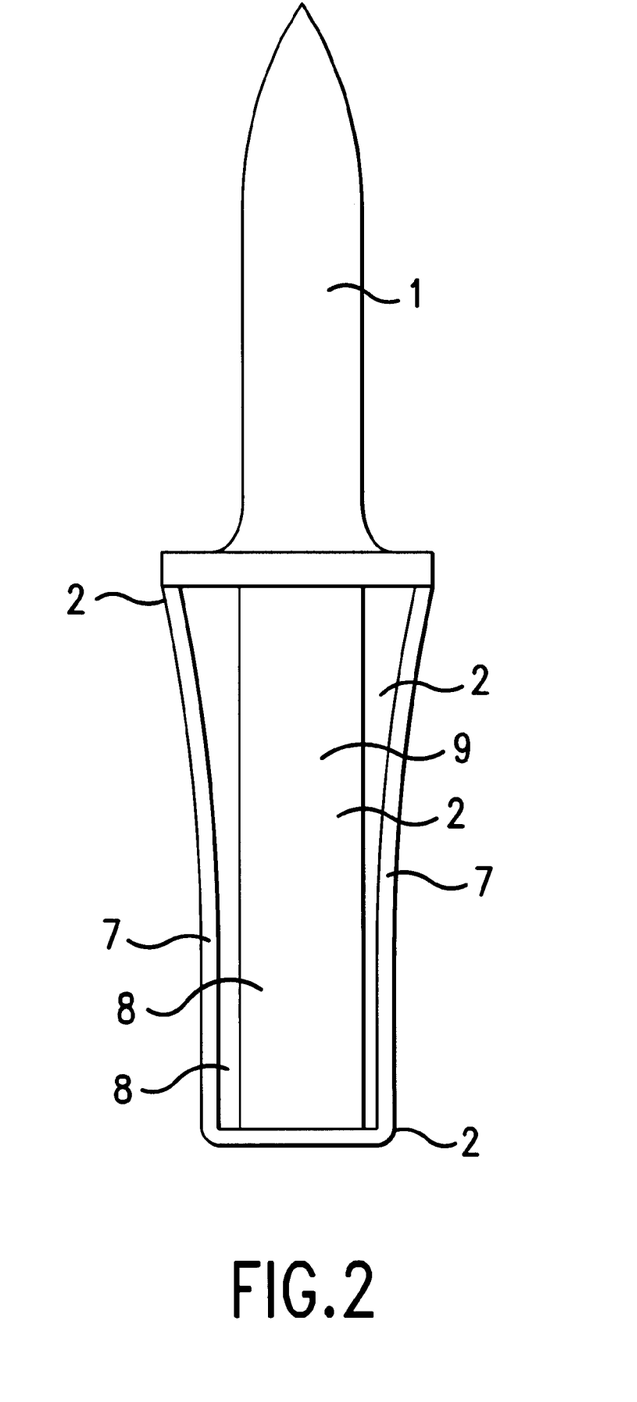
FIG. 2 depicts the perforating analytical test device viewed from the side on which the back wall connecting the two handle walls of the grip portion is shown.

FIG. 2 shows another side view of the stopper perforating device. In FIG. 2 the sharp-pointed tip portion (1) and the handle portion (2) are shown. The aperture and recess are not shown from this point of view of the tip portion (1). In the grip portion (2) the back wall (8) provided with a niche (9), and which supports the test stick and connects the two handle walls (7) is shown. In the grip portion (2) the niche (9) is shaped or molded to fit the form of the test stick. Said niche (9), which is shaped or formed by the back wall (8) is made to facilitate the insertion of the test stick, when it is pushed down into tip portion (1) through the opening (not shown in FIG. 2) in the tip portion (1). Beside the niche (9), the back wall (8), forming a support to the test stick is shown.

Figure 3:
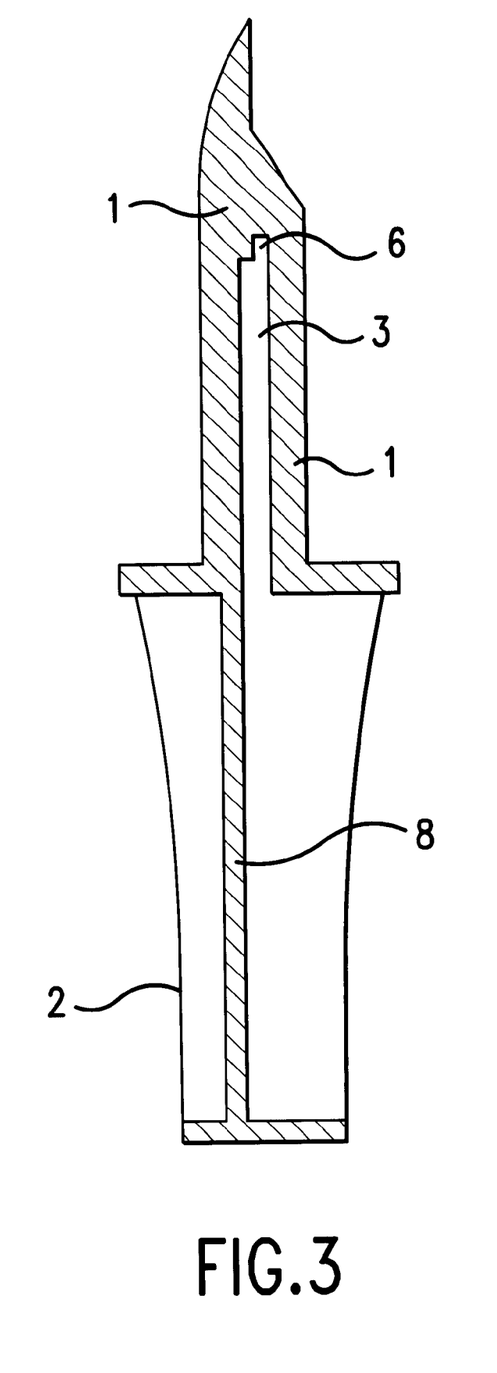
FIG. 3 depicts a longitudinal section of the perforating analytical test device in which the back wall connecting the handle walls of the grip portion is shown in the center and the inner side of the opposite handle wall is indicated. The opening into which the test stick is placed or can be placed as well as the recess is also shown.

FIG. 3 depicts a longitudinal section of the perforating analytical test device with the sharp-pointed tip clearly shown in the tip portion (1) and the handle walls of the grip portion (2). The tip portion (1) contains an optionally rectangular opening (3) for the test stick. The opening (3) continues as a recess (6) into which the test stick cannot reach, but which facilitates free flow of the sample solution. In the grip portion (2) the back wall (8) supporting the test stick can be seen. The niche is not indicated in FIG. 3. The test stick is inserted along the supporting back wall (8) of the grip portion (2) and then into the bottom of the opening (3) in the tip portion (1) leaving the recess (6) empty, which in turn facilitates free contact between the test stick and the sample solution to be absorbed into the wetting zone of the test stick.

Figure 4:
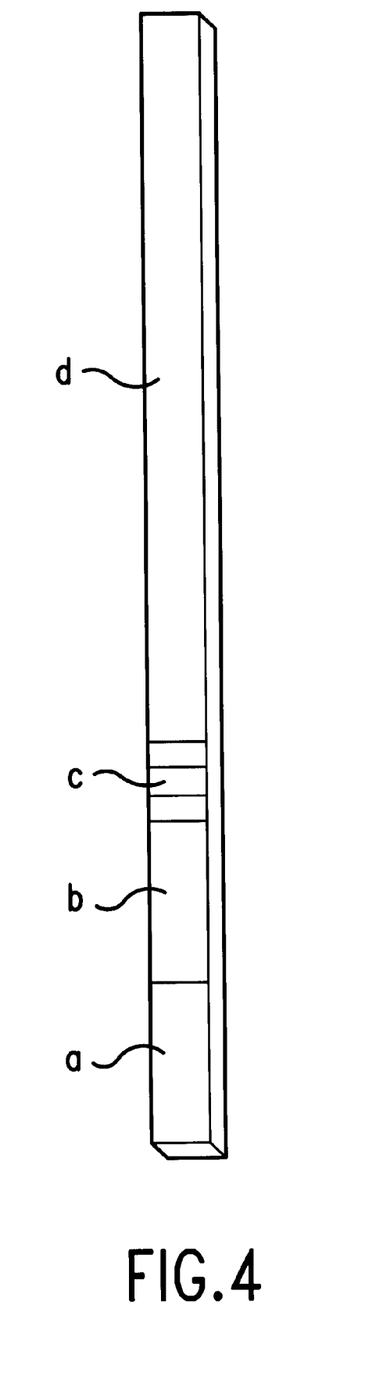
FIG. 4 depicts a separate test stick, with four optional zones. The test sticks can either be placed into the device during the manufacturing procedure or which can be sold separately and placed before use into the opening specifically provided in the perforating analytical test device by the person performing the test.

FIG. 4 shows a separate test stick, which can be inserted into the stopper perforating device. The test stick comprises a wetting zone (a), a zone incorporating tracers preferably labelled with particulate visible markers (b), a reading zone (c) and a zone (d), into which any redundant or excess sample solution is absorbed.

Figure 5:
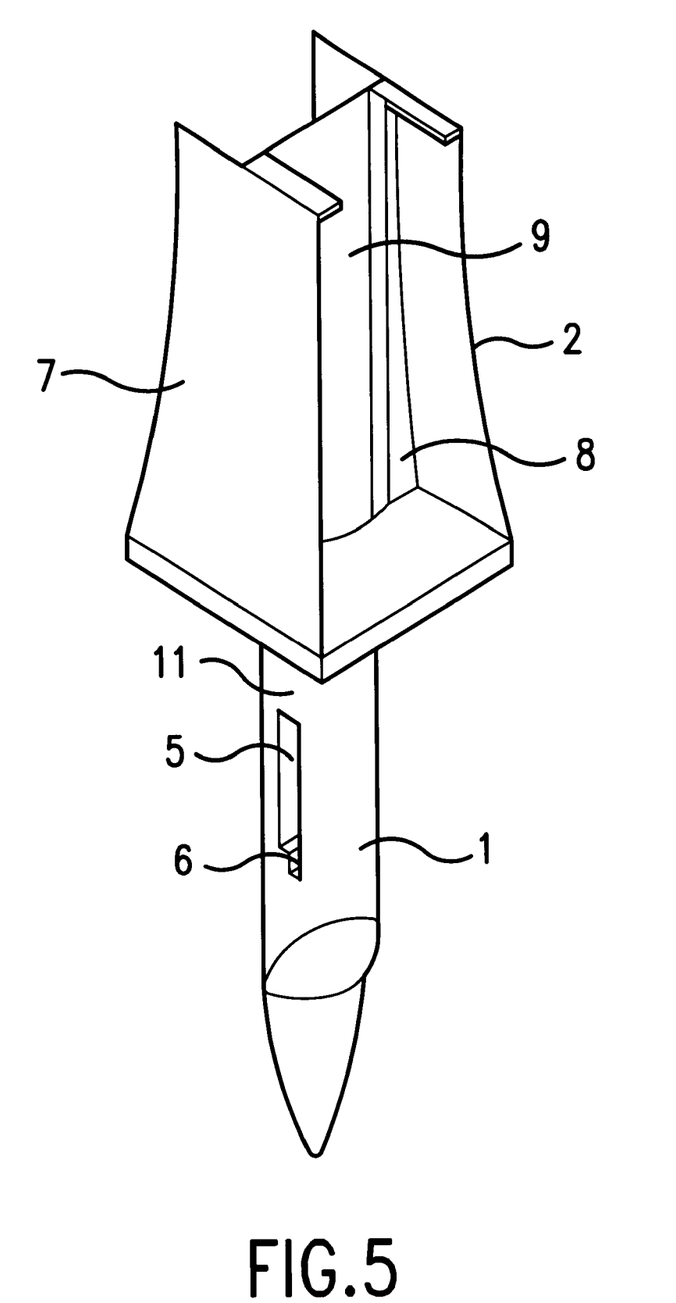
FIG. 5 depicts a perforating analytical test device without the test stick. The handle walls and the back wall with the niche is shown as well as the tip portion with the aperture and recess.

FIG. 5 shows a perforating analytical test device, without any test stick. FIG. 5 shows the tip portion (1) with the aperture (5) continuing into the recess (6), from which the sample solution is absorbed into the test stick. The supporting back wall (8) with the niche (9) for the test stick connecting the two handle walls are shown.

Figure 6:
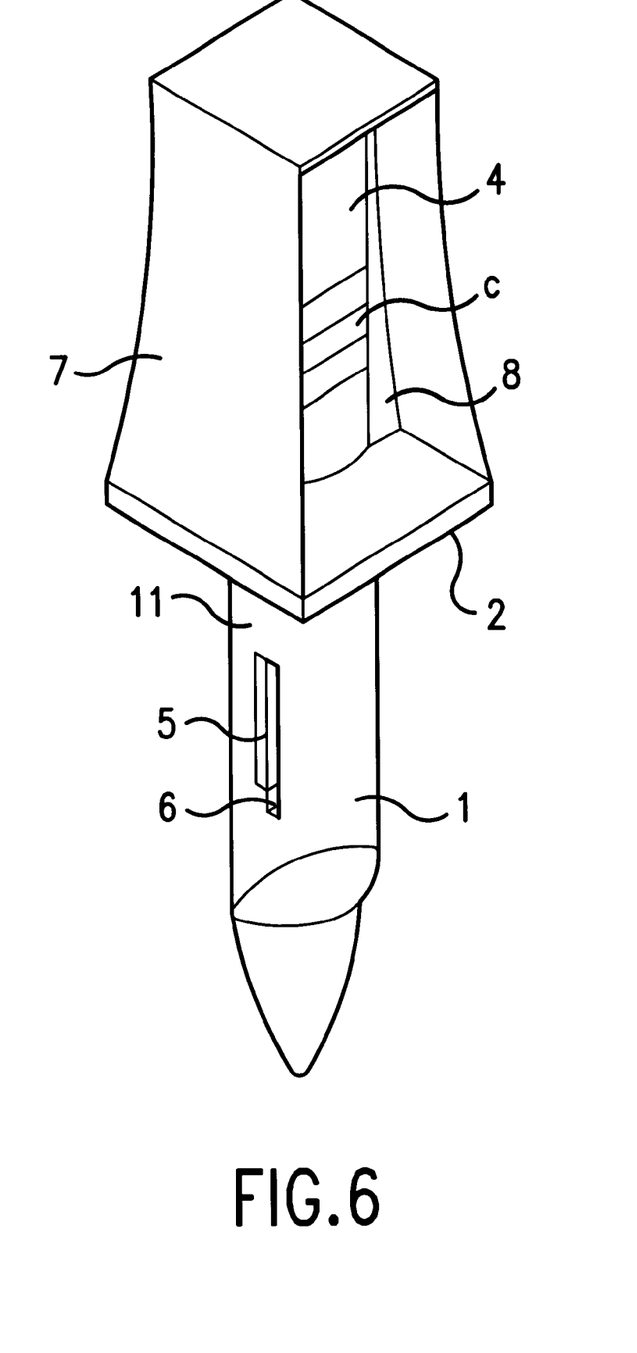
FIG. 6 depicts a closed model of the perforating analytical test device with a test stick, which has been placed into the opening in tip portion (not shown) during the manufacturing procedure. The reading zone of the test stick is seen in the niche in the back wall of the grip portion in said closed model of the device.

FIG. 6 shows the perforating analytical test device with a ready fitted test stick (4). The upper side of perforating device can optionally be closed as indicated in FIG. 6, but the device can be open as well. In FIG. 6 the tip portion (1) and the grip portion (2) are shown. In the tip portion (1), the aperture (5), the length of which is not longer than the wetting region of the test stick continues as a small recess (6) or hole, into which the test stick does not reach, but from which the sample solution is absorbed into the wetting zone of test stick (4).

Figure 7:
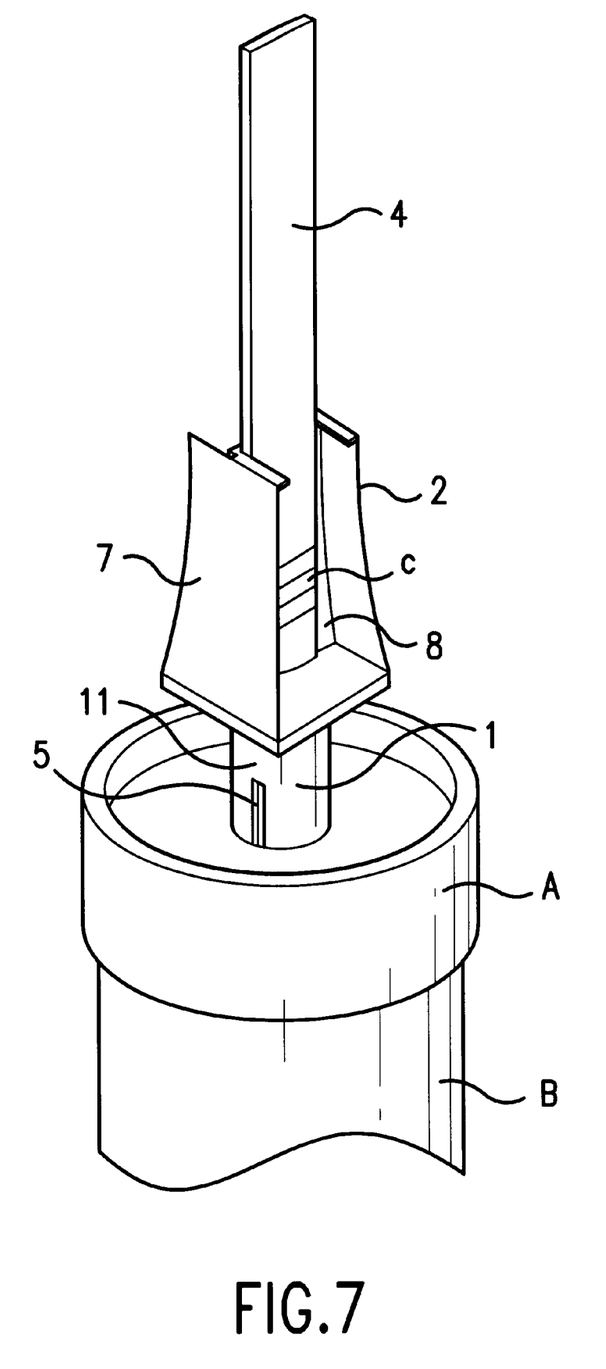
FIG. 7 depicts the perforating analytical test device into which the person performing the test has placed a separate test stick. Part of the aperture can be seen in the grip portion, which has partly penetrated the stopper.

FIG. 7 shows a perforating analytical test device, which has partly perforated a stopper. The grip portion (2) contains a test stick (4) inserted by the person performing the test. The reading zone (c) and the grip portion (2) protrudes out from the stopper of the perforating analytical test device. In the reading zone (c) the presence of lines indicate the results, generally interpretable as yes or no. The tip portion (1) of the perforating analytical test device has not been pushed completely through the stopper (A) of the sampling vessel (B). As a consequence the aperture (5) on the tip portion of the stopper perforating device can still be seen. The region (11) between the aperture (5) and the starting point of grip portion (2) indicates an area which can be used to enable a certain mobility of the perforating analytical test device, if it is desired to push the device so that it contacts the sample solution for a while and then pull it up to break the contact. When the test is carried out the aperture (5) on the outside of the tip portion should be totally inside the sampling vessel (B) to avoid any contamination.

Figure 8:
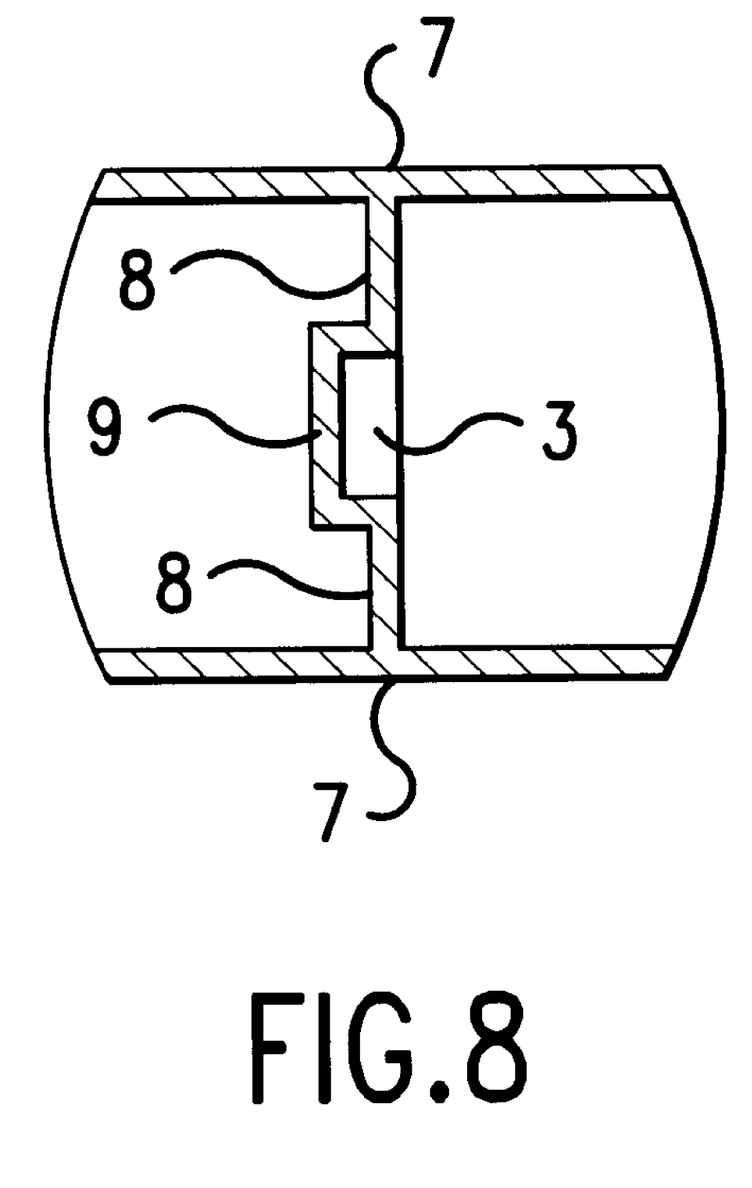
FIG. 8 depicts a cross-sectional view from the central part of the perforating analytical test device with an opening for the test stick passing through the middle of the device.

FIG. 8 shows a cross-section of the perforating analytical test device just in the center or middle of the device between the tip and grip portions viewed from above looking down into the tip portion. In FIG. 8 the sides correspond to the handle walls (7). In the middle of FIG. 8 the supporting shaped or molded back wall (8) forms the so called niche (9), which further supports the test stick.

Figure 9:
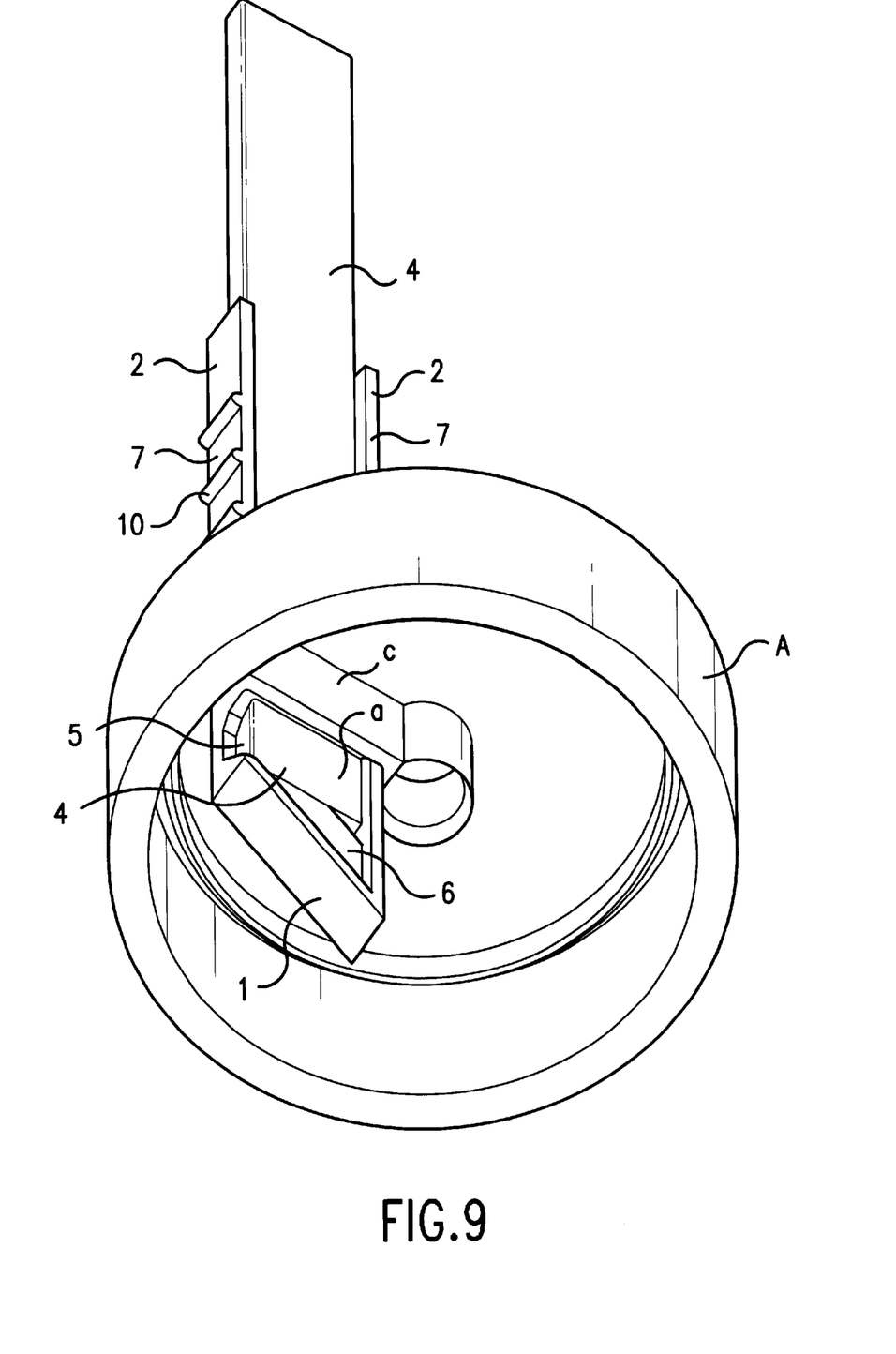
FIG. 9 depicts a stopper seen from below with the perforating analytical test device with an alternative design. The device has penetrated the stopper through an area on the stopper, especially designed to assist the perforation. The area can be provided with some auxiliary supporting structures.

FIG. 9 shows a perforating analytical test device with an alternative design and a stopper provided with an area with supporting structures (C). The device has penetrated the stopper (A) and is viewed from below the stopper. The tip portion (1) is optionally open and provided with an aperture (5) and recess (6) even if it is not so important in the open model. The grip portion (2) with the handle walls (7) are shown above the stopper. Hold improving means (10) in form of protruding stripes are shown on the left handle wall (7).

Figure 10:
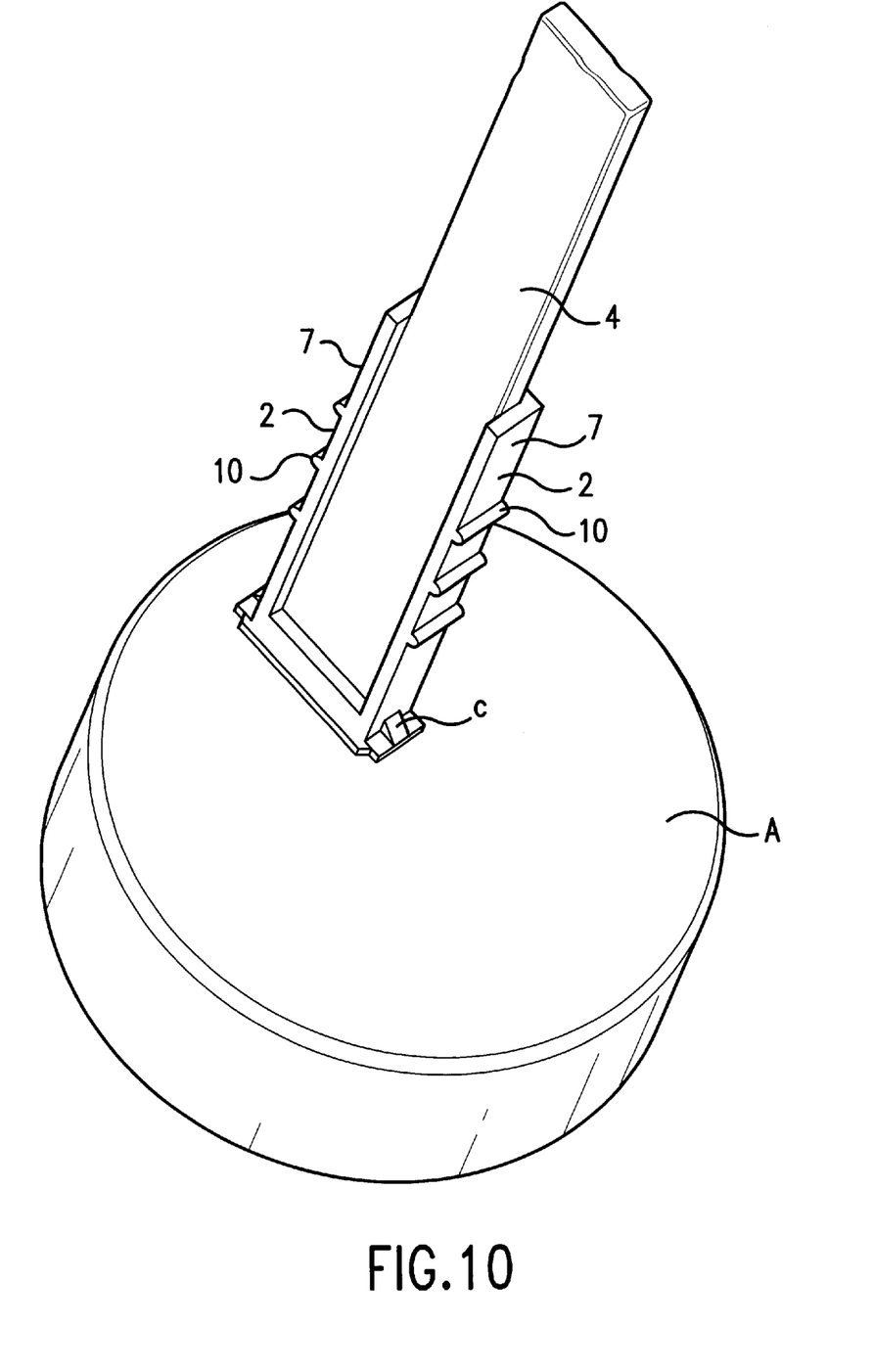
FIG. 10 depicts the perforating analytical test device with the alternative design. The device is shown, when it has penetrated the stopper through the specially designed area. The device is seen from the upper side of the stopper.

FIG. 10 shows the perforating analytical test device of FIG. 9 from above. The test stick (4) is inserted into the perforating analytical test device and the device has penetrated the stopper (A) through the area, which is made of softer and more elastic material and has been provided with supporting structures (C).

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A perforating analytical test device for handling sample solutions comprising:
   a sharp pointed tip portion insertable into a sample solution and an opposite end for receiving a test means;
   the tip portion having an aperture in communication with a recess that is between the aperture and the opposite end wherein the recess is open to the ambient environment through the aperature and the opposite end whereby a portion of a sample solution can flow through the aperature into the recess without vacuum or applied pressure; and a grip portion connected to the opposite end such that the recess is not occluded when the testing means is inserted in the opposite end and the test means can be viewed.

2. The device of claim 1, wherein the test means is a test stick when inserted into the device through the opposite end into the recess will simultaneously be in communication with the aperture and opposite end, the test stick being detachable from the test device.

3. The device of claim 1, wherein the test means is a test stick when inserted into the device through the opposite end into the recess will simultaneously be in communication with the aperture and opposite end, the test stick being mounted in and affixed to the test device.

4. The device of claim 1, wherein the tip portion is capable of penetrating a sampling vessel or a stopper of a sampling vessel and wherein the recess is adjacent the aperture and opening and is sized such that the test means is not positionable therein.

5. The device of claim 1, further comprising hold improving means for the grip portion, the hold improving means including at least one of nibbles, protuberances and a roughened surface.

6. The device of claim 1, further comprising a test means with a wetting zone and wherein the aperture in the tip portion is no longer than the wetting zone of the test stick.

7. The device of claim 1, wherein the test device is used with a sampling vessel and wherein the test device includes a test means with a wetting zone, dimensions of the test device are such that the wetting zone of the test means can be contacted with a sample in the sampling vessel for a predetermined period of time.

8. The device of claim 1, wherein the grip portion further includes two handle walls and a test means supporting back wall, the two handle walls being connected by the back wall.

9. The device of claim 8, wherein the grip portion further includes a niche shaped to facilitate support of the test means.

10. The device of claim 1, further comprising a test means with a reading zone, the reading zone being visible when the test stick is inserted in the test device.

11. The device of claim 10, wherein the tip portion is capable of penetrating a sampling vessel or a stopper of a sampling vessel and wherein the reading zone protrudes from and is visible outside the sampling vessel or the stopper and wherein the grip portion further includes a niche shaped to facilitate support of the test stick.

12. The device of claim 1, wherein the device is produced for a material sufficiently strong and durable for perforation of a sampling vessel or stopper and sufficiently elastic and flexible for a water-tight joint between the test device and the sampling vessel or the stopper.

13. The device of claim 12, wherein the device is made from plastics.

14. The device of claim 1, wherein the test device is a part of an analytical test kit which includes separately packed perforating test devices and test means, the test sticks being insertable into the test device before use.

15. The device of claim 14, wherein the test devices are disposable and wherein the test means are preinserted in the test device before packaging such that the test devices are ready for use.

16. A method for performing an analytical test using a test device having a tip portion and a grip portion, the method comprising the steps of:

providing the test device with a test means, the test means extending from the grip portion to the tip portion of the test device;

penetrating the sampling vessel or stopper on a sampling vessel with the tip portion of the test device wherein the test device comprises a sharp pointed tip portion insertable into a sample solution and an opposite end for receiving the test means;

the tip portion having an aperture in communication with a recess that is between the aperture and the opposite end wherein the recess is open to the ambient environment through the aperture and the opposite end whereby a portion of a sample solution can flow through the aperture into the recess without vacuum or applied pressure;

a grip portion connected to the opposite end such that the recess is not occluded when the testing means is inserted in the opposite end and the test results from the testing means can be viewed; and contacting a sample solution in the sampling vessel with the test means through an aperture in the tip portion;

absorbing the sample solution through the aperture into the test means for a time sufficient for the sample solution to reach the reading zone of the test means; and monitoring a result from the test device by viewing the reading zone of the test means.

17. The method of claim 16, further comprising the step of destroying the sampling vessel and test device after the step of monitoring, the sampling vessel remaining closed through the step of destroying whereby a person using the test device is not exposed to the sample solution.

18. The method of claim 16, wherein the test means is test stick having a wetting zone and a reading zone such that the reading zone is visible during the step of monitoring.

19. The method of claim 18, further comprising the step of turning the sampling vessel up-side down until the sample is absorbed in the wetting zone of the test strip and reaches the reading zone and thereafter turning the sampling vessel into an up-right position until a result is readable from the reading zone of the test strip.

20. The method of claim 18, further comprising the step of avoid excess absorption of the sample solution by pushing the test device into contact with the sample solution and when the sample solution is absorbed through the wetting zone and reaches the reading zone in the test stick, the test device is pulled out of contact with the sample solution to break contact therebetween, the aperture of the tip portion of the testing device remaining inside the sampling vessel or stopper of the sampling vessel after the test device is pulled out of contact.

* * * * *